US011166775B2

(12) United States Patent
Gilhooley et al.

(10) Patent No.: US 11,166,775 B2
(45) Date of Patent: Nov. 9, 2021

(54) ROBOTIC CUTTING SYSTEMS AND METHODS FOR SURGICAL SAW BLADE CUTTING ON HARD TISSUE

(71) Applicant: MAKO Surgical Corp., Ft. Lauderdale, FL (US)

(72) Inventors: Seamus Gilhooley, Galway (IE); David Gene Bowling, Los Ranchos De Albuquerque, NM (US); Paul Shiels, Albuquerque, NM (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 265 days.

(21) Appl. No.: 16/131,400

(22) Filed: Sep. 14, 2018

(65) Prior Publication Data

US 2019/0083191 A1    Mar. 21, 2019

Related U.S. Application Data

(60) Provisional application No. 62/559,096, filed on Sep. 15, 2017.

(51) Int. Cl.
*A61B 34/00* (2016.01)
*A61B 34/32* (2016.01)
(Continued)

(52) U.S. Cl.
CPC ............ *A61B 34/70* (2016.02); *A61B 17/142* (2016.11); *A61B 17/155* (2013.01); *A61B 34/30* (2016.02);
(Continued)

(58) Field of Classification Search
CPC ....... A61B 17/14; A61B 17/142; A61B 17/15; A61B 17/154; A61B 17/155; A61B 17/16;
(Continued)

(56) References Cited

U.S. PATENT DOCUMENTS 7,691,106 B2 *  4/2010  Schenberger ........ A61B 17/142
                                                    606/82
7,725,162 B2    5/2010  Malackowski et al.
(Continued)

FOREIGN PATENT DOCUMENTS

EP    2889015 A1    7/2015
EP    3001963 A2    4/2016
(Continued)

OTHER PUBLICATIONS

International Search Report for Application No. PCT/US2018/051313 dated Mar. 11, 2019, 5 pages.
(Continued)

*Primary Examiner* — Si Ming Ku
(74) *Attorney, Agent, or Firm* — Howard & Howard Attorneys PLLC

(57) ABSTRACT

A robotic cutting system including a robotic manipulator and a cutting tool coupled to the robotic manipulator. The cutting tool comprises a saw blade. A controller is also coupled to the robotic manipulator. The controller is configured to control operation of the robotic manipulator, the cutting tool, and/or another cutting tool, to cut the bone in an initial stage of cutting until a notch is created in the bone at a predetermined depth. A final stage of cutting is then completed by cutting along the cutting plane.

21 Claims, 9 Drawing Sheets

(51) Int. Cl.
*A61B 34/30* (2016.01)
*A61B 17/14* (2006.01)
*A61B 17/15* (2006.01)
*A61B 90/00* (2016.01)
*A61B 17/16* (2006.01)
*A61B 17/00* (2006.01)

(52) U.S. Cl.
CPC ............. *A61B 34/32* (2016.02); *A61B 17/15* (2013.01); *A61B 2017/00477* (2013.01); *A61B 2017/1602* (2013.01); *A61B 2090/062* (2016.02); *A61B 2090/067* (2016.02); *A61B 2090/08021* (2016.02); *G05B 2219/45117* (2013.01); *G05B 2219/45171* (2013.01)

(58) Field of Classification Search
CPC . A61B 2017/1602; A61B 34/30; A61B 34/32; A61B 34/70; G05B 2219/45117; G05B 2219/45144; G05B 2219/45171
See application file for complete search history.

(56) References Cited

U.S. PATENT DOCUMENTS

| | | | |
|---|---|---|---|
| 8,010,180 B2 * | 8/2011 | Quaid | A61N 1/0534 600/424 |
| 8,608,745 B2 | 12/2013 | Guzman et al. | |
| 8,894,654 B2 * | 11/2014 | Anderson | A61B 17/17 606/80 |
| 8,992,534 B2 * | 3/2015 | Lee | A61B 17/1633 606/80 |
| 9,084,613 B2 * | 7/2015 | Qutub | A61B 17/16 |
| 9,119,655 B2 | 9/2015 | Bowling et al. | |
| 9,226,796 B2 * | 1/2016 | Bowling | B25J 9/1633 |
| 9,566,122 B2 | 2/2017 | Bowling et al. | |
| 2005/0234465 A1 | 10/2005 | McCombs et al. | |
| 2009/0287222 A1 | 11/2009 | Lee et al. | |
| 2010/0106511 A1 | 4/2010 | Shirakawa et al. | |
| 2011/0130761 A1 | 6/2011 | Plaskos et al. | |
| 2012/0330429 A1 | 12/2012 | Axelson, Jr. et al. | |
| 2014/0180290 A1 | 6/2014 | Otto et al. | |
| 2017/0348007 A1 | 12/2017 | Shiels | |

FOREIGN PATENT DOCUMENTS

| | | | |
|---|---|---|---|
| WO | 2013179053 A1 | 12/2013 | |
| WO | WO-2017139674 A1 * | 8/2017 | G01L 3/08 |

OTHER PUBLICATIONS

Communication Relating to the Results of the Partial International Search for PCT/US2018/051313 dated Jan. 14, 2019, 2 pages.

* cited by examiner

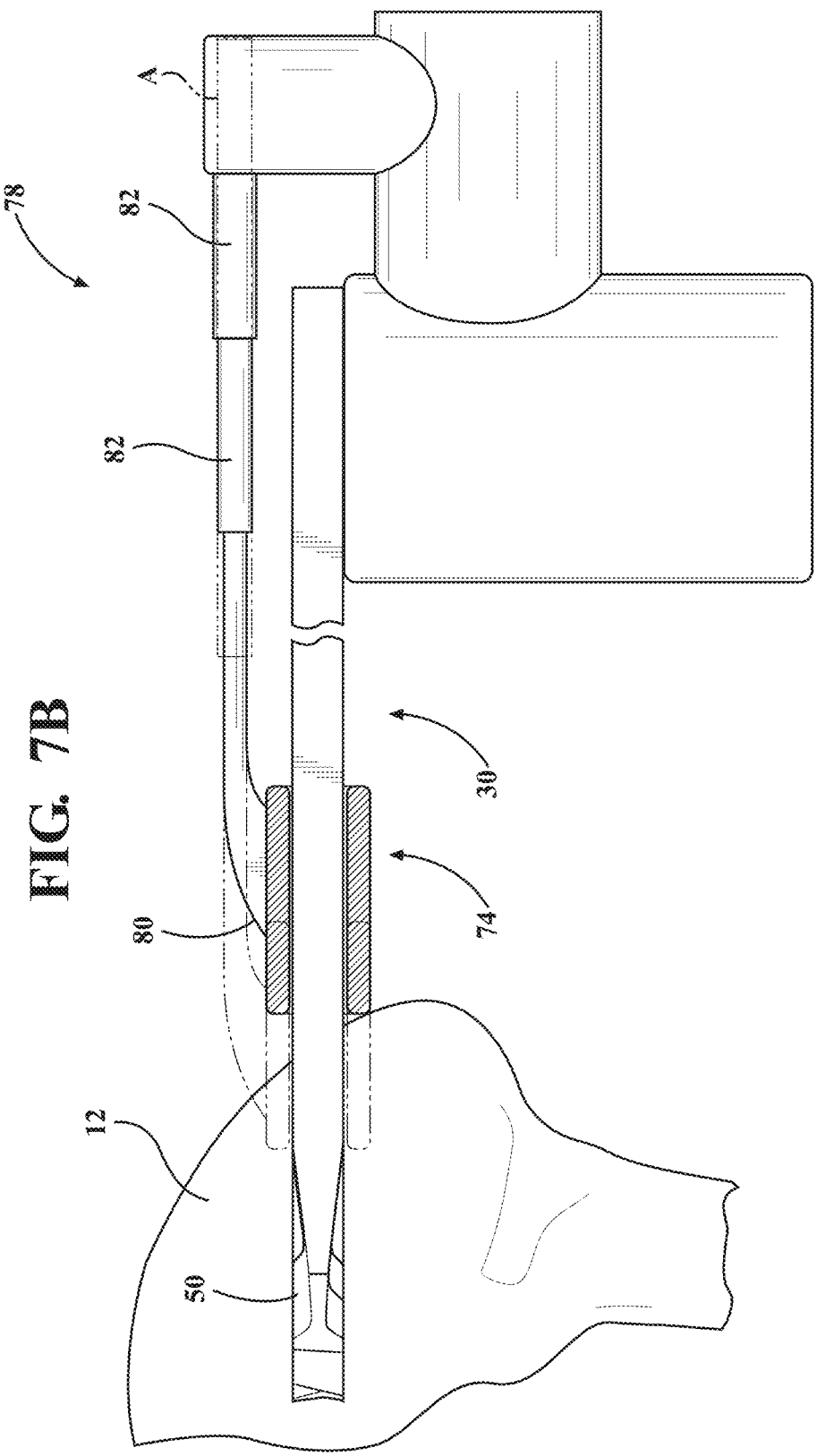

ROBOTIC CUTTING SYSTEMS AND METHODS FOR SURGICAL SAW BLADE CUTTING ON HARD TISSUE

RELATED APPLICATION

This application claims the benefit of and priority to U.S. Provisional Patent Application No. 62/559,096, filed on Sep. 15, 2017, the disclosure of which is hereby incorporated herein by reference.

TECHNICAL FIELD

The embodiments described herein generally relate to robotic cutting systems and methods of use thereof.

BACKGROUND

It is prevalent to use powered surgical saws during surgical procedures. Generally, these surgical saws may be operated by a user such as a surgeon or may be operated by a robotic cutting system. The surgical saws include a saw blade which is configured to cut hard tissue of a patient, such as bone. For example, saw blades are used in total knee arthroplasty, total hip arthroplasty, and similar types of procedures to create planar cuts on the bone.

In conventional surgical saws, undesirable skiving (e.g., deviation from an intended cut plane and/or deviation from an intended entry point) occurs during the cutting process, and specifically during the initial cut of the hard tissue with the saw blade. Skiving can be particularly difficult to control when making an initial cut on non-flat portions of hard tissue, such as at the ends of a femur (e.g., condyles, femur head). Skiving often includes undesirable flexing of the saw blade away from the desired location of the initial cut. One option to reduce skiving is to employ a cutting guide for the saw blade to hold the saw blade in place while making the necessary cuts. However, using cutting guides can increase the length of time it takes to make the necessary cuts because it requires that the cutting guide first be secured to the bone at the desired location. Additionally, the use of cutting guides often require the use of longer blades, which can still introduce skiving effects. In robotic surgery, one of the goals is to increase cutting accuracy and reduce cutting time, which can be difficult in cases where the saw blade is unable to initially cut at a desired location.

A robotic cutting system for controlling a surgical saw in a manner that overcomes one or more of the aforementioned challenges is desired.

SUMMARY

In one embodiment, a robotic cutting system is provided. The robotic cutting system comprises a robotic manipulator and a cutting tool to be coupled to the robotic manipulator. The cutting tool has a blade configured to cut a bone along a cutting plane. A controller is coupled to the robotic manipulator to control the robotic manipulator and the cutting tool to perform an initial stage of cutting along an initial plane prior to performing a final stage of cutting along the cutting plane. The initial plane is at a different orientation than the cutting plane. The controller is configured to control the robotic manipulator and the cutting tool to facilitate cutting along the initial plane with the blade to create a notch for the blade and to facilitate reorienting the blade from the initial plane to the cutting plane.

In another embodiment, a robotic cutting system is provided. The robotic cutting system comprises a robotic manipulator and a cutting tool to be coupled to the robotic manipulator. The cutting tool has a blade configured to cut a bone along a cutting plane. A controller is coupled to the robotic manipulator to control the robotic manipulator to reciprocate the blade along the cutting plane to create a notch for the blade prior to resecting the bone along the cutting plane.

In another embodiment, a robotic cutting system is provided. The robotic cutting system comprises a robotic manipulator and a cutting tool to be coupled to the robotic manipulator. The cutting tool has a blade configured to cut a bone along a cutting plane. The robotic cutting system also comprises a bur to be coupled to the robotic manipulator. A controller is coupled to the robotic manipulator to control the robotic manipulator to perform an initial stage of burring a notch into the bone for the blade prior to performing a final stage of cutting along the cutting plane with the blade.

In another embodiment, a robotic cutting system is provided. The robotic cutting system comprises a robotic manipulator and a cutting tool to be coupled to the robotic manipulator. The cutting tool has a blade configured to cut a bone along a cutting plane. A controller is coupled to the robotic manipulator to control the robotic manipulator to perform cutting along the cutting plane. A blade guide is coupled to the robotic manipulator. The controller is configured to control the robotic manipulator and the cutting tool to facilitate cutting along the cutting plane while guiding the blade with the blade guide. The blade guide is capable of retracting as the blade penetrates into the bone along the cutting plane.

A method of cutting bone using a robotic cutting system is also provided. The method comprises controlling a robotic manipulator and a cutting tool to facilitate cutting along an initial plane with a blade to create a notch for the blade and to facilitate reorienting the blade from the initial plane to a cutting plane, the initial plane being at a different orientation than the cutting plane.

Another method of cutting bone using a robotic cutting system is provided. The method comprises controlling a robotic manipulator to reciprocate a blade along a cutting plane to create a notch for the blade prior to the bone being resected along the cutting plane.

Another method of cutting bone using a robotic cutting system is provided. The method comprises controlling a robotic manipulator to burr a notch into the bone for receiving a blade prior to resecting the bone along a cutting plane with the blade.

Another method of cutting bone using a robotic cutting system is provided. The method comprises controlling a robotic manipulator and a cutting tool to facilitate cutting along a cutting plane while guiding a blade with a retractable blade guide retracting the blade guard as the blade penetrates into the bone along the cutting plane.

BRIEF DESCRIPTION OF THE DRAWINGS

Advantages of the present disclosure will be readily appreciated as the same becomes better understood by reference to the following detailed description when considered in connection with the accompanying drawings wherein:

FIG. 7B is a side view of the cutting tool of the robotic cutting system having the blade guide in a retracted position.

DETAILED DESCRIPTION

Figure 1:
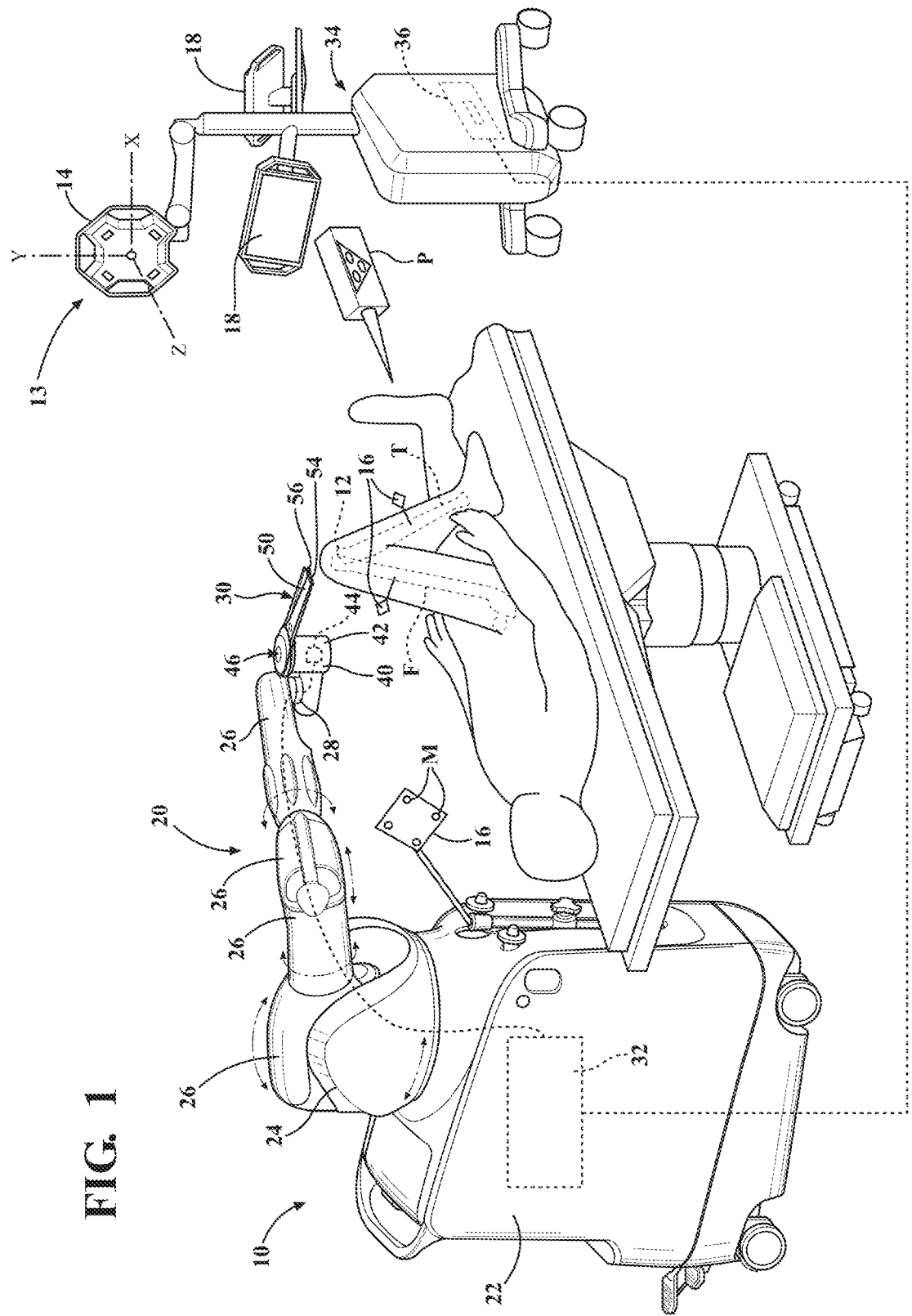
FIG. 1 is a perspective view of a robotic cutting system in an operating room.

Referring to the Figures, a robotic cutting system 10 is shown for use during surgical procedures. The surgical procedures may be orthopedic surgeries, brain surgeries, or any other surgeries requiring the use of a cutting instrument. Typically, the surgical procedure will include the cutting of hard tissue 12, such as bone or the like. In some embodiments, the surgical procedure involves partial or total knee, hip, or shoulder replacement surgery, or may involve spine surgery.

The robotic cutting system 10 is designed to cut away material. In some cases, the material (e.g., bone) is to be replaced by surgical implants such as hip, knee, shoulder, and spine implants, including unicompartmental, bicompartmental, or total knee implants, acetabular cups, femur stems, humerus implants, and the like. Some of these types of implants are disclosed in U.S. Patent Application Publication No. 2012/0330429, entitled, "Prosthetic Implant and Method of Implantation," the entire disclosure of which is hereby expressly incorporated by reference herein. It should be appreciated that the systems and methods disclosed herein may be used to perform other procedures, surgical or non-surgical, or may be used in industrial applications or other applications.

The robotic cutting system 10 comprises a navigation system 13 including a localizer 14 and tracking devices 16, one or more displays 18, and a robotic manipulator comprising a robotic arm 20 and a base 22. The robotic arm 20 includes a base link 24 rotatably coupled to the base 22 and a plurality of arm links 26 serially extending from the base link 24 to a distal end 28. The arm links 26 pivot/rotate about a plurality of joints in the robotic arm 20. A cutting tool 30 is connected to the distal end 28 of the robotic arm 20. The robotic arm 20 may be capable of moving the cutting tool 30 in multiple degrees of freedom, e.g., five or six degrees of freedom.

A robotic controller 32 is coupled to the robotic manipulator to provide control of the robotic arm 20 or guidance to the surgeon during manipulation of the cutting tool 30. In one embodiment, the robotic controller 32 is configured to control the robotic arm 20 (e.g., joint motors thereof) to provide haptic feedback to the user via the robotic arm 20. This haptic feedback helps to constrain or inhibit the surgeon from manually manipulating (e.g., moving) the cutting tool 30 beyond predefined virtual boundaries associated with the surgical procedure. Such a haptic feedback system and associated haptic objects that define the virtual boundaries are described, for example, in U.S. Pat. No. 8,010,180, which is hereby incorporated by reference herein in its entirety. In one embodiment, the robotic cutting system 10 comprises the RIO™ Robotic Arm Interactive Orthopedic System manufactured by MAKO Surgical Corp. of Fort Lauderdale, Fla., USA.

In some embodiments, the robotic arm 20 acts autonomously based on predefined tool paths and/or other predefined movements to perform the surgical procedure. Such movements may be defined during the surgical procedure and/or before the procedure. In further embodiments, a combination of manual and autonomous control is utilized. For example, a robotic system that employs both a manual mode in which a user manipulates the cutting tool 30 by applying force to the cutting tool 30 to cause movement of the robotic arm 20 and a semi-autonomous mode in which the user holds a pendant to control the robotic arm 20 to autonomously follow a tool path is described in U.S. Pat. No. 9,566,122, hereby incorporated by reference herein in its entirety.

The navigation system 13 is set up to track movement of various objects in the operating room. Such objects include, for example, the cutting tool 30, the patient's anatomy of interest, e.g., the femur F and tibia T, and/or other objects. The navigation system 13 tracks these objects for purposes of displaying their relative positions and orientations to the surgeon and, in some cases, for purposes of controlling or constraining manual manipulation of the cutting tool 30 relative to virtual boundaries associated with the patient's anatomy.

The navigation system 13 includes a cart assembly 34 that houses a navigation controller 36. The navigation controller 36 and the robotic controller 32 collectively form a control system of the robotic cutting system 10. A navigation interface is in operative communication with the navigation controller 36. The navigation interface includes the displays 18 that are adjustably mounted to the cart assembly 34. Input devices such as a keyboard and mouse can be used to input information into the navigation controller 36 or otherwise select/control certain aspects of the navigation controller 36. Other input devices are contemplated including a touch screen (not shown) or voice-activation.

The localizer 14 communicates with the navigation controller 36. In the embodiment shown, the localizer 14 is an optical localizer and includes a camera unit (one example of a sensing device). The camera unit has an outer casing that houses one or more optical position sensors. In some embodiments at least two optical sensors are employed, sometimes three or more. The optical sensors may be separate charge-coupled devices (CCD). The camera unit is mounted on an adjustable arm to position the optical sensors with a field of view of the below discussed tracking devices 16 that, ideally, is free from obstructions. In some embodiments the camera unit is adjustable in at least one degree of freedom by rotating about a rotational joint. In other embodiments, the camera unit is adjustable about two or more degrees of freedom.

The localizer 14 includes a localizer controller (not shown) in communication with the optical sensors to receive signals from the optical sensors. The localizer controller communicates with the navigation controller 36 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors communicate directly with the navigation controller 36.

Position and orientation signals and/or data are transmitted to the navigation controller 36 for purposes of tracking the objects. The cart assembly 34, the displays 18, and the localizer 14 may be like those described in U.S. Pat. No. 7,725,162 to Malackowski, et al. issued on May 25, 2010, entitled "Surgery System," hereby incorporated by reference.

The navigation controller 36 can be a personal computer or laptop computer, or any other suitable form of controller. Navigation controller 36 has the displays 18, central processing unit (CPU) and/or other processors, memory (not shown), and storage (not shown). The navigation processors can be any type of processor, microprocessor or multi-processor system. The navigation controller 36 is loaded with software as described below. The software converts the signals received from the localizer 14 into data representative of the position and orientation of the objects being tracked.

Navigation system 13 includes the plurality of tracking devices 16, also referred to herein as trackers. In the illustrated embodiment, trackers 16 are coupled to separate bones of the patient, e.g., the femur F and tibia T. In some cases, the trackers 16 are firmly affixed to sections of bone via bone screws, bone pins, or the like. In other cases, clamps on the bone may be used to attach the trackers 16. In further embodiments, the trackers 16 could be mounted to other tissue types or parts of the anatomy. The position of the trackers 16 relative to the anatomy to which they are attached can be determined by registration techniques, such as point-based registration in which a digitizing probe P (e.g., navigation pointer) is used to touch off on bony landmarks on the bone or to touch on several points on the bone for surface-based registration. Conventional registration techniques can be employed to correlate the pose of the trackers 16 to the patient's anatomy, e.g., the bones being treated.

A base tracker 16 is also coupled to the base 22 to track the pose of the cutting tool 30, e.g., when combined with data derived from joint encoders in the joints of the robotic arm 20 that partially define the spatial transformation from the base 22 to the distal end 28 of the robotic arm, and when combined with data describing the location of the cutting tool 30 with respect to the distal end 28. In other embodiments, a separate tracker 16 could be fixed to the cutting tool 30, e.g., integrated into the cutting tool 30 during manufacture or may be separately mounted to the cutting tool 30 in preparation for the surgical procedure. In any case, a working end of the cutting tool 30 is being tracked by virtue of the base tracker 16 or other tracker. The working end may be a distal end of an accessory of the cutting tool 30. Such accessories may comprise a saw blade 50, such as an oscillating saw blade.

In the illustrated embodiment, the trackers 16 are passive trackers. In this embodiment, each tracker 16 has at least three passive tracking elements or markers M for reflecting light from the localizer 14 back to the optical sensors. In other embodiments, the trackers 16 are active trackers and may have light emitting diodes or LEDs transmitting light, such as infrared light to the optical sensors. Based on the received optical signals, navigation controller 36 generates data indicating the relative positions and orientations of the trackers 16 relative to the localizer 14. In some cases, more or fewer markers may be employed. For instance, in cases in which the object being tracked is rotatable about a line, two markers can be used to determine an orientation of the line by measuring positions of the markers at various locations about the line. It should be appreciated that the localizer 14 and trackers 16, although described above as utilizing optical tracking techniques, could alternatively, or additionally, utilize other tracking modalities to track the objects, such as electromagnetic tracking, radio frequency tracking, ultrasound tracking, inertial tracking, combinations thereof, and the like.

Figure 2:
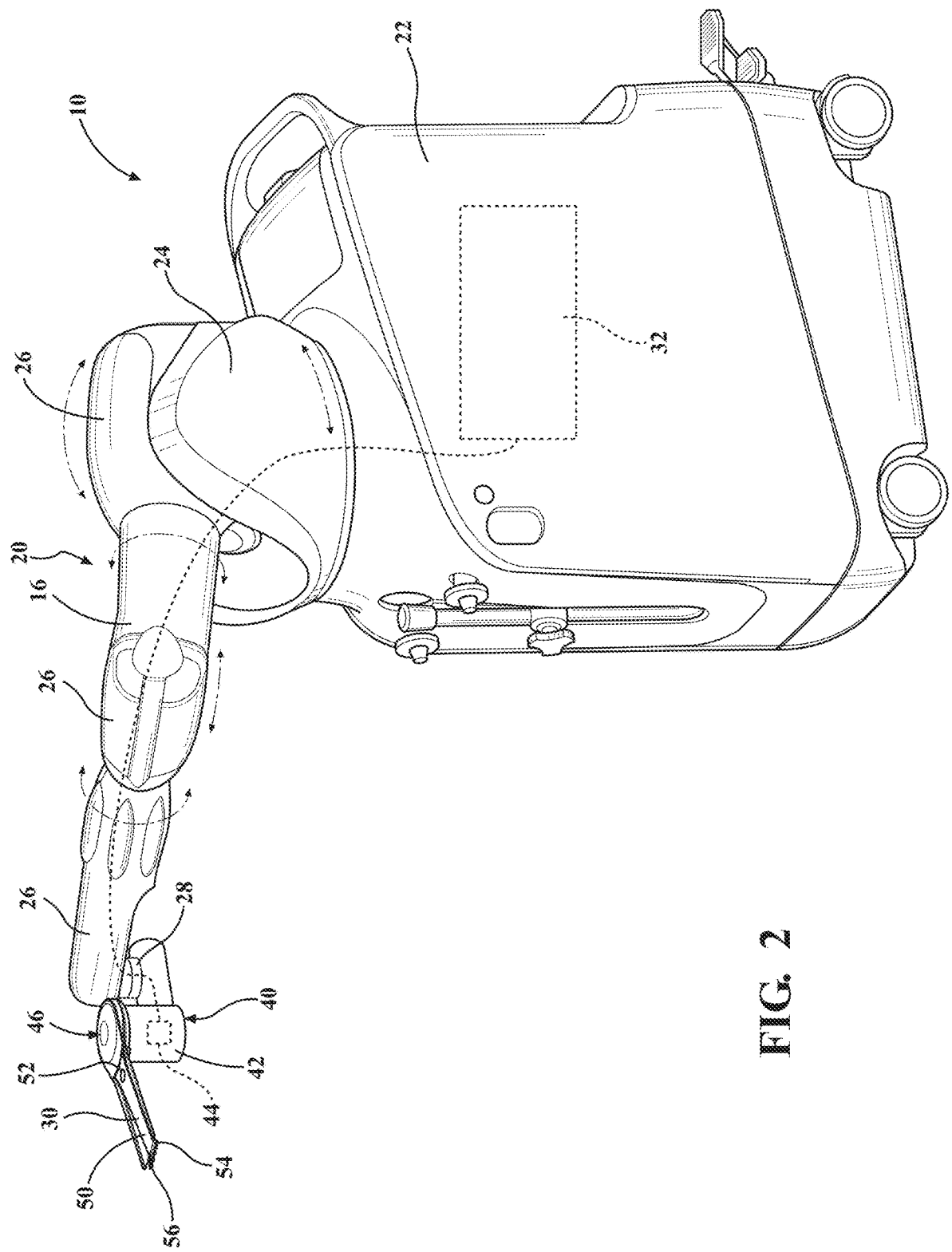
FIG. 2 is a perspective view of the robotic cutting system.

In some embodiments, such as the embodiment illustrated in FIG. 2, the cutting tool 30 includes a coupler 40 having a housing 42 for attaching to the robotic manipulator. It is also contemplated that a separate motor 44 may be located in the housing 42 of the coupler 40. The motor 44 may be of any suitable type to operate the cutting tool 30, including but not limited to a pneumatic or electrical motor. The motor 44 is configured, for instance, to provide oscillating motion to the saw blade 50 of the cutting tool 30 during the surgical procedure. It is contemplated that the motor 44 may provide cyclical linear motion and/or cyclical angular motion, such as used for an oscillating sagittal saw. In some embodiments, the cutting tool 30 may include a drive hub 46 coupled to the motor 44.

The saw blade 50 may be of any size, shape, or type (i.e. straight blade, crescent blade, etc.). The saw blade 50 includes an attachment portion 52 configured to be removably coupled to the housing 42. Opposite the attachment portion 52, the saw blade 50 includes a cutting portion 54 which has a plurality of teeth 56. In some embodiments, the saw blade 50 is formed from a single piece of material, such as metal, by stamping and/or machining. The saw blade 50 may be configured to create a kerf with a generally flat face or may be configured to provide a kerf with a rounded profile. However, various configurations have been contemplated. The cutting tool 30 and associated saw blade 50 may be like that described in U.S. Patent Application Pub. No. 2017/0348007, filed on Jun. 2, 2017, entitled "Surgical Saw and Saw Blade for use therewith," which is hereby incorporated herein by reference. The cutting tool 30 and associated saw blade 50 may also be like that described in U.S. Patent Application Pub. No. 2014/0180290, filed on Dec. 21, 2012, entitled "Systems and Methods for Haptic Control of a Surgical Tool," which is hereby incorporated herein by reference.

Referring now to FIGS. 3A through 7B, a desired cutting plane 66 is defined as the plane in which a planar cut is desired to be made with the saw blade 50. In the embodiments illustrated, the cutting plane 66 is disposed transverse to an outer surface of the hard tissue 12. More specifically, the outer surface of the hard tissue 12 (e.g., bone) is arcuate or curved such that the cutting plane 66 often extends non-perpendicularly from the outer surface. As a result, merely placing the saw blade 50 on the cutting plane 66, starting oscillation of the saw blade 50, and then making contact with the outer surface to initiate cutting, without more, will likely result in skiving of the saw blade 50 along the curved outer surface. The systems and methods described herein are intended to limit such skiving.

In these systems and methods, virtual objects (such as virtual boundaries), which may also be haptic objects (such as haptic boundaries), may be used to control (e.g., limit and/or constrain) movement of the saw blade 50 by operating the robotic arm in a desired manner to limit skiving. These virtual/haptic objects may be defined by points, lines, planes, volumes, or the like, and may be 1-D, 2-D, or 3-D. Such virtual/haptic objects may be defined as models and could be solid models (e.g., built with constructive solid geometry or the like), surface models (e.g., surface mesh, etc.), or any suitable form of 3-D model. These objects may be registered pre-operatively or intraoperatively to images/models (e.g., CT scans, X-ray images, MRI images, 3-D models, etc.) of the patient's anatomy that are mapped to the patient's actual anatomy using well-known registration techniques. Thus, in some embodiments, the locations of the virtual/haptic objects described herein are mapped to the patient's anatomy to control movement of the saw blade 50 in a manner that limits skiving of the saw blade 50. For example, the robotic cutting system 10 may be controlled based on a haptic boundary that defines a desired plane in which the saw blade 50 should be constrained. In this case, the robotic controller 32 operates the robotic arm 20 so that the saw blade is confined by the haptic boundary to stay on the desired plane. The manner of controlling the robotic cutting system, e.g., the robotic arm 20, based on such virtual/haptic objects is described, for example, in U.S. Pat. Nos. 8,010,180, 9,119,655, or U.S. Patent Application Pub. No. 2014/0180290, all of which are hereby incorporated herein by reference.

In some procedures, such as during a total knee procedure, several planar cuts are made to the hard tissue 12, and any of these planar cuts may employ the methods described herein. In some embodiments, cutting may be completely through the hard tissue 12 or only partially through the hard tissue 12 such that the cut is finished when a pre-determined final depth is reached. The cutting plane 66 may be defined pre-operatively by the surgeon, such as by defining desired planar cuts on a virtual 3-D model of the hard tissue 12 created using pre-operative images taken of the hard tissue. The desired planar cuts may also be defined by the shape of the implant and a 3-D model of the implant. The cutting plane 66 may be defined intraoperatively by the surgeon, or automatically by the control system. A position and orientation of the cutting plane 66 may be tracked by the navigation system 13 as the hard tissue 12 moves during the surgical procedure by virtue of the tracker 16 attached to the hard tissue 12 and registration of the tracker 16 to the hard tissue 12. The location of the cutting plane 66 may be tracked by virtue of being mapped to the 3-D model that includes the cutting plane 66. The robotic manipulator can accommodate movement of the cutting plane 66 and autonomously adjust its own positioning as needed to maintain any desired relationship to the hard tissue 12 required in the methods described herein, such as staying on a desired plane with respect to the hard tissue 12 when necessary. Such control may be accomplished using the robotic controls described, for example, in U.S. Pat. Nos. 8,010,180, 9,119, 655, or U.S. Patent Application Pub. No. 2014/0180290, all of which are hereby incorporated herein by reference.

Figure 3A:
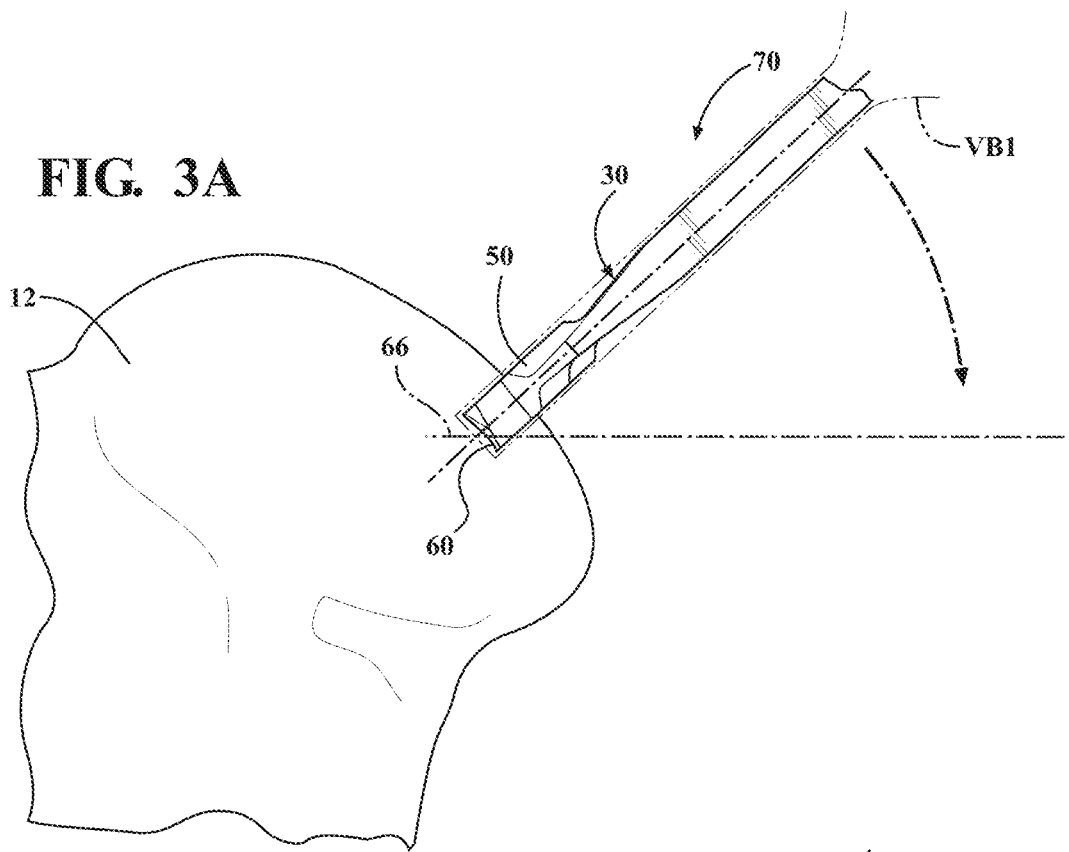
FIG. 3A is a side view of a cutting tool of the robotic cutting system according to one embodiment in a first orientation.
Figure 3B:
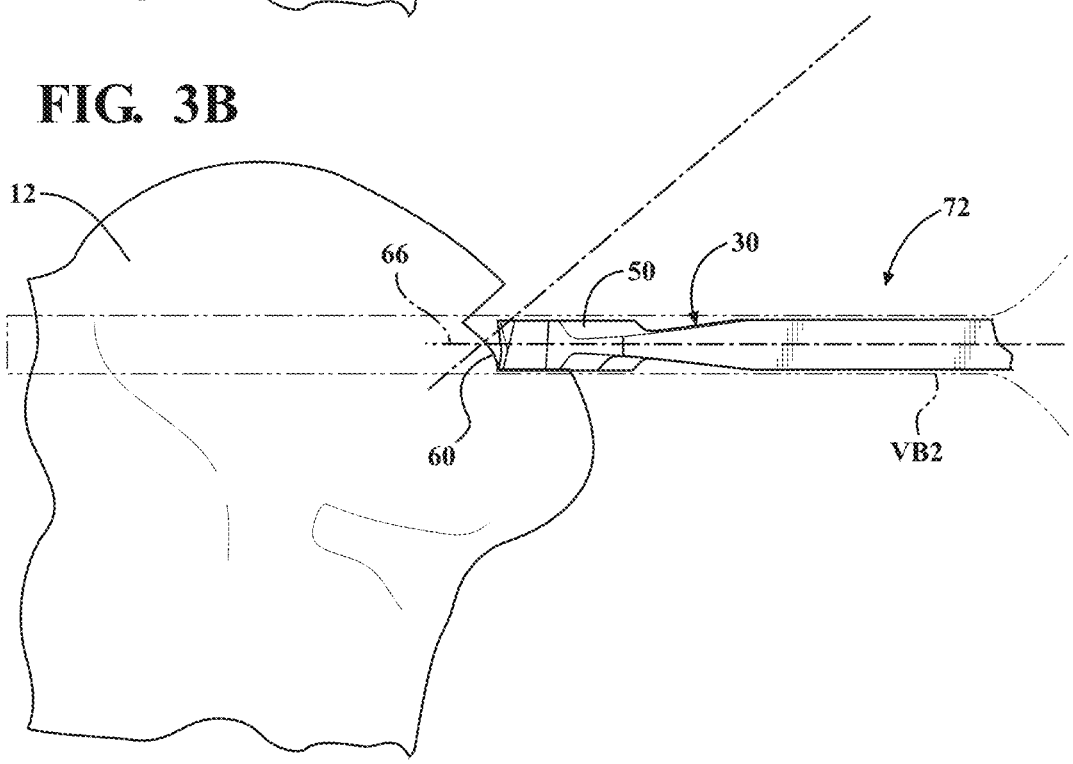
FIG. 3B is a side view of the cutting tool of the robotic cutting system according to one embodiment in a second orientation.

Referring to FIGS. 3A and 3B, one system and method for limiting skiving of the saw blade 50 is illustrated. In this embodiment, the robotic cutting system 10 begins the cut with the saw blade 50 in a first orientation 70 which is normal to the outer surface of the hard tissue 12 in the vicinity of the cutting plane 66. The saw blade 50 remains in the first orientation 70 until the cut reaches a predetermined depth. It is also contemplated that the first orientation 70 may be any position not in-line with the cutting plane 66 that provides an advantage in reducing skiving of the saw blade 50. The predetermined depth may be any depth, but is typically enough depth to create an initial notch 60 (also referred to as a groove) in the hard tissue 12. Once the notch 60 is created, the saw blade 50 is reoriented (e.g., articulated) to a second orientation 72 (see FIG. 3B), in line with the cutting plane 66, and the cut is finished. The notch 60 is used to create a fulcrum in the hard tissue 12 about which the saw blade 50 is able to pivot from the first orientation 70 to the second orientation 72.

In operation, the cutting tool 30 is first coupled to the robotic manipulator. The control system is configured to control movement of the cutting tool 30 via the robotic manipulator. The control system may comprise a tool controller for operating the motor 44 of the cutting tool 30 to facilitate cutting. The tool controller may comprise part of the robotic controller 32, or be separate from the robotic controller 32. When the cutting tool 30 is coupled to the robotic manipulator, and the user is ready to begin cutting along the cutting plane 66, the control system will send a command to the robotic arm 20 (e.g., to control the joint motors thereof) to move the cutting tool 30 so that the saw blade 50 is first located on (e.g., aligned with) an initial plane associated with the first orientation 70 (FIG. 3A). The saw blade 50 is aligned with the initial plane by being in the same general orientation as the initial plane with the initial plane passing through or being adjacent to the saw blade 50. In other embodiments, the user may position the cutting tool 30 at the first orientation 70 by virtue of haptic guidance as described herein. The user may be able to operate the robotic cutting system 10 to move the cutting tool 30 so that the saw blade 50 is automatically aligned with the initial plane in the first orientation in the manner described in U.S. Patent Application Pub. No. 2014/0180290, which is incorporated herein by reference. The robotic cutting system 10, by virtue of the navigation system 13 and associated trackers 16, and/or by virtue of the encoders in the joints of the robotic arm 20, is able to determine the position and orientation of the saw blade 50 with respect to the initial plane to locate the saw blade 50 as required. In some versions, the initial plane passes through an intersection of the cutting plane 66 and the outer surface of the hard tissue 12, but is normal to the outer surface of the hard tissue 12 at the intersection. Accordingly, by orienting the saw blade 50 generally normal to the outer surface of the hard tissue 12, skiving can be limited during cutting. A current position of the saw blade 50 and/or the desired position of the saw blade 50 relative to the patient's anatomy may be represented on a display and updated in real-time so that the user is able to visualize when the saw blade 50 is in the desired position (e.g. in the first orientation on the initial plane).

Once at the first orientation 70, the control system then operates the motor 44 to start oscillating the saw blade 50 to begin the initial cut to the outer surface of the hard tissue 12. The control system may automatically start oscillation, or this may be in response to user input (e.g., a trigger). The saw blade 50 is then moved along the initial plane toward the hard tissue 12 to form the notch 60. Movement of the cutting tool 30 toward the hard tissue 12 to make the initial cut can be done autonomously or manually. One or more virtual boundaries (e.g., a virtual plane) may be activated to define the first orientation 70 to keep the cutting tool 30 on the initial plane associated with the first orientation 70 and to prevent the user from cutting beyond the initial notch 60 that is needed (e.g., the virtual boundary may be limited in depth). The same virtual boundaries can also be used to provide haptic guidance to the user to initially locate the saw blade 50 on the initial plane associated with the first orientation 70. For example, a virtual boundary (e.g., virtual plane) with a width only slightly larger than the saw blade 50 (to accommodate for oscillations) and a depth at the depth of the initial notch 60 may be programmed into the control system so that any attempt by the user to manually move the saw blade 50 outside of the boundary (e.g., off the plane and/or deeper than the initial notch 60) results in haptic feedback from the robotic manipulator in the same manner described in U.S. Pat. No. 8,010,180, incorporated herein by reference.

One example of a virtual boundary VB1 to align the saw blade 50 with the initial plane is shown in FIG. 3A in the form of a bounded volume that defines the initial plane. The virtual boundary VB1 has a thickness about the thickness of the saw blade 50 to constrain the saw blade 50 from moving away from the first orientation 70, a width (not shown) which is about the same as the width of the saw blade 50 (when oscillating) to avoid any unnecessary lateral movement, an open starting end (so that the saw blade 50 can enter the virtual boundary VB1), and a closed target end at the desired depth of the notch 60. The virtual boundary VB1 can be mapped with respect to the hard tissue 12 pre-operatively or intra-operatively using registration techniques for mapping the model of the virtual boundary VB1 to the 3-D model of the hard tissue 12. Alternatively, the user could locate the virtual boundary VB1 manually on a user interface connected to the navigation controller 36. Such virtual boundaries may also be haptic boundaries that operate to limit or constrain movement of the saw blade 50 and provide haptic feedback to the user in the event the saw blade 50 is being moved in a manner that violates, or will violate, the boundary.

Once the predetermined depth is reached and the initial notch 60 is formed, the saw blade 50 is autonomously reoriented by the robotic manipulator (or manually by the user) to the second orientation 72 in line with the cutting plane 66, as illustrated in FIG. 3B. Thus, the virtual boundary VB1 may be deactivated and a separate virtual boundary associated with the second orientation 72 may be activated to keep the saw blade 50 on the cutting plane 66 during manual cutting. The saw blade 50 then finishes the cut through the hard tissue 12 along the cutting plane 66.

It is contemplated that the saw blade 50 may continue cutting during reorientation from the first orientation 70 to the second orientation 72 such that the notch 60 has an arcuate shape. In this case, the teeth of the saw blade 50 may be arranged to cut the hard tissue 12 in multiple directions, including in the direction of reorientation to form the notch 60. However, it is also contemplated that the blade 50 may be removed from the hard tissue 12 and then reoriented to the second orientation 72 before finishing the cut along the cutting plane 66—in this case a small ridge of bone left from cutting along the initial plane may first be encountered by the saw blade 50 before it reaches the notch 60, which may cause a slight deflection of the saw blade 50, but then the notch 60 acts to capture the saw blade 50 and keep it on the cutting plane 66.

To facilitate movement from the first orientation 70 and the initial plane to the second orientation 72 and the cutting plane 66, an intermediate virtual boundary may be provided that extends from the initial plane to the cutting plane so that the user in unable to move the saw blade 50 beyond either plane, but is allowed to freely reorient the saw blade 50 manually. In one version, the distal end of the saw blade 50 pivots in the notch 60 from the first orientation and the initial plane to the second orientation and the cutting plane. The robotic cutting system 10 may also operate to automatically move the saw blade 50 from the initial plane to the cutting plane 66 in the same manner that the control system in U.S. Patent Application Pub. No. 2014/0180290, which is incorporated herein by reference, automatically aligns the saw blade. Thus, such motion may be manual or autonomous. Another virtual boundary may be activated once the saw blade 50 is aligned with the cutting plane 66 to restrict movement of the saw blade 50 to along the cutting plane 66. This virtual boundary may also be a haptic boundary that limits or constrains movement of the saw blade 50 to the cutting plane 66. An example of this virtual boundary is illustrated as virtual boundary VB2 in FIG. 3B, which is shown as a volume, similar to the virtual boundary VB1.

Figure 4:
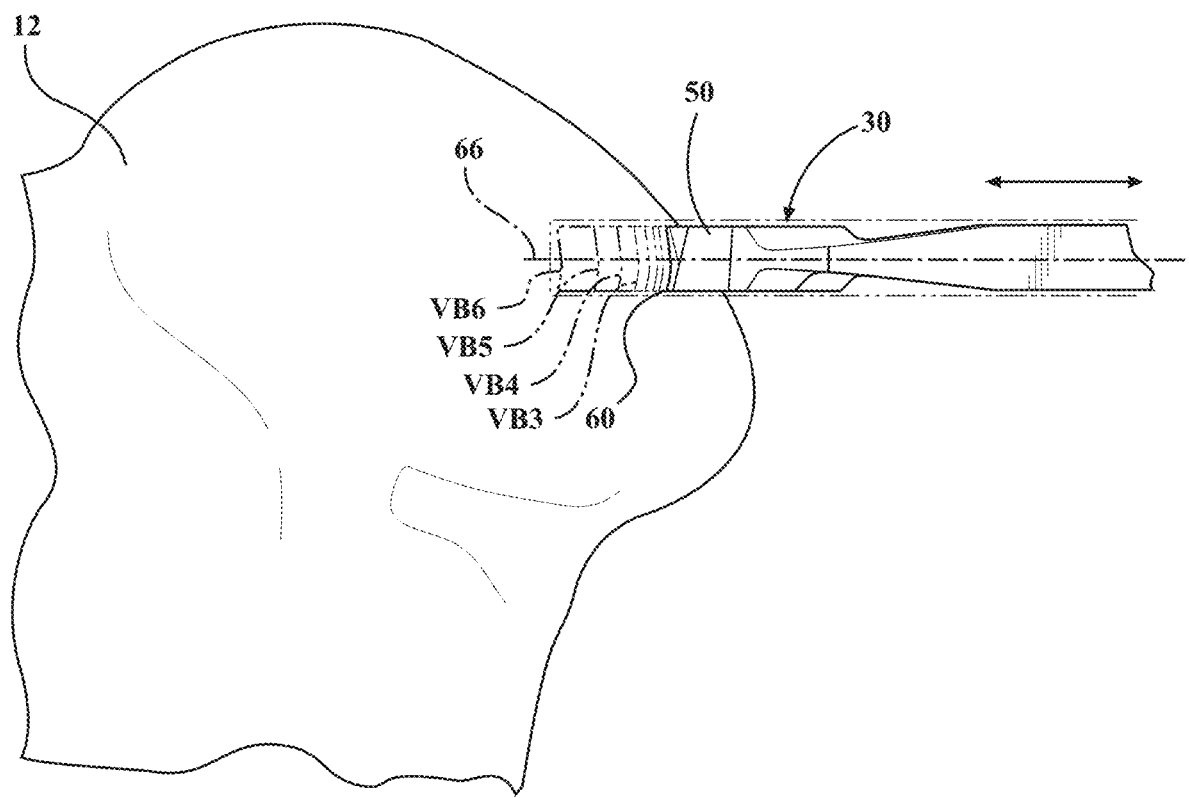
FIG. 4 is a side view of the cutting tool of the robotic cutting system according to another embodiment.

In another embodiment, illustrated in FIG. 4, the cutting tool 30 is initially placed in line with the cutting plane 66 (either autonomously or manually with virtual objects). For instance, the user may be able to operate the robotic cutting system 10 to move the cutting tool 30 so that the saw blade 50 is automatically aligned with the cutting plane 66 in the manner described in U.S. Patent Application Pub. No. 2014/0180290, which is incorporated herein by reference. Once on the cutting plane 66, the cutting tool 30 is reciprocated to form the initial notch 60 in the hard tissue 12. This reciprocating motion (also referred to as pecking) may be carried out autonomously or manually as well. This reciprocating motion may be defined as motion axially along a longitudinal axis of the blade, e.g., reciprocating lengthwise. If carried out autonomously, the robotic manipulator is configured to move the cutting tool 30 and its saw blade 50 along the cutting plane 66 at incrementally increasing depth, in combination with slight retractions, to effectively chip away at the outer surface of the hard tissue 12 to limit skiving that could otherwise occur if attempting to start cutting at a non-perpendicular orientation to the curved surface. In this case, the autonomous movement creates the reciprocating motion needed to form the initial notch 60 in the hard tissue 12 such that the saw blade 50 is capable of being captured in the notch to limit skiving. The saw blade 50 may be constrained to stay on the cutting plane 66 via one or more virtual boundaries associated with each of the reciprocations (e.g., the virtual boundary dynamically changes to increase the depth as hard tissue is removed, or new virtual boundaries are created after each contact made with the hard tissue 12). An example of an initial virtual boundary VB3 for the first peck at the hard tissue 12 and sequentially created virtual boundaries VB4, VB5, VB6 for subsequent pecks at the hard tissue 12 are shown in FIG. 4. Once the initial peck is made with the robotic cutting system 10 using the virtual boundary VB3, then virtual boundary VB3 is deactivated and virtual boundary VB4 is activated to penetrate into the hard tissue 12 slightly further, and so on, until the notch 60 is formed.

In some versions, the reciprocation is carried out by actuating the joint motors of the robotic manipulator in a manner that causes the saw blade 50 to reciprocate. This can be accomplished by activating the joint motors so that the saw blade 50 remains aligned with the cutting plane 66, yet translates along the cutting plane 66 back and forth a desired distance and at a desired frequency. In other versions, the cutting tool 30 has a reciprocating feature to reciprocate the saw blade 50 along its cutting plane. In this version, the robotic manipulator merely places the distal end of the saw blade 66 at an interface with the outer surface of the hard tissue 12 on the cutting plane 66 and the tool controller then activates the cutting tool 30 to begin its reciprocating motion to peck the hard tissue 12 and form the notch 60.

Ultimately, during reciprocation, the saw blade 50 repeatedly contacts the hard tissue 12 with repeating force to form the initial notch 60 at the predetermined depth. In other words, the saw blade 50 pecks at the hard tissue 12 using the force to produce the notch 60. Two, three, four, or more sequential reciprocations may be needed to form the initial notch 60 in the bone. The robotic controller 32 may control the robotic manipulator so that the reciprocations may be conducted at frequencies of one reciprocation every second, one every millisecond, or the like. The duration, frequency, and depth of such reciprocations (including distance of retracting away from the hard tissue 12) may vary as needed to create the initial notch 60. Forces could also be monitored during such reciprocations so that the force applied on the hard tissue 12 by the robotic manipulator during pecking is kept at or below certain thresholds. In some embodiments, the saw blade 50 is oscillating during the reciprocation. Once the predetermined depth is reached, the control system is configured to continue oscillation of the saw blade 50 and control the saw blade 50 to finish the cut along the cutting plane 66 as previously described, e.g., without reciprocating, such as to resect a portion of the bone. In other embodiments, the reciprocating motion is carried out while the saw blade 50 is stationary with respect to the housing 42, e.g., the saw blade 50 is not oscillating.

Additionally, the oscillating speed of the blade tip (which oscillates laterally on the cut plane), in some cases decreases, increases or otherwise varies during the creation of the notch, or during the pecking motion. This reduces the lateral reaction forces exerted on the bone, until the blade is sufficiently captured/constrained inside the bone by the bone material. The control system is configured to control and vary the oscillating speed in any desired manner, including automatically varying the speed according to a predetermined speed profile. For example, the oscillating speed may start at an initial speed much slower than a normal oscillating speed, and then increase a predetermined percentage (e.g., 5% or more, 10% or more, 20% or more, 50% or more, etc.) for every subsequent peck or reciprocation until at normal oscillating speed. Other speed profiles may be used.

Figure 5A:
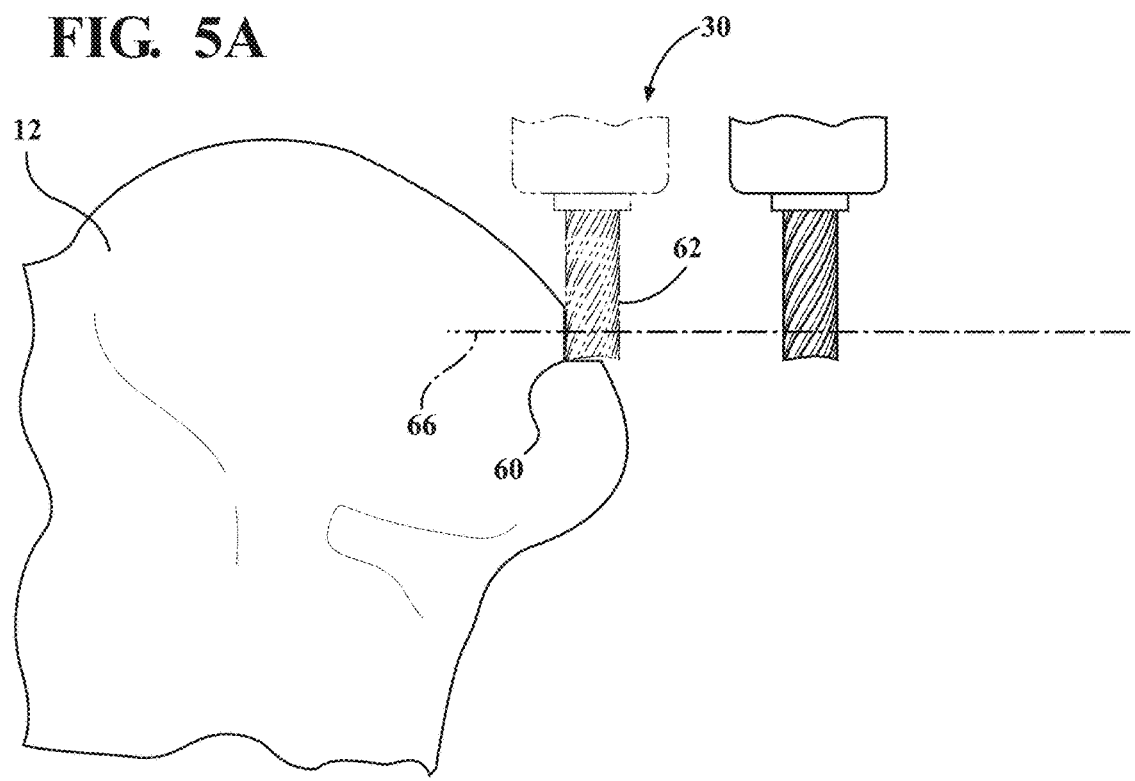
FIG. 5A is a side view of the cutting tool of the robotic cutting system according to yet another embodiment.
Figure 5B:
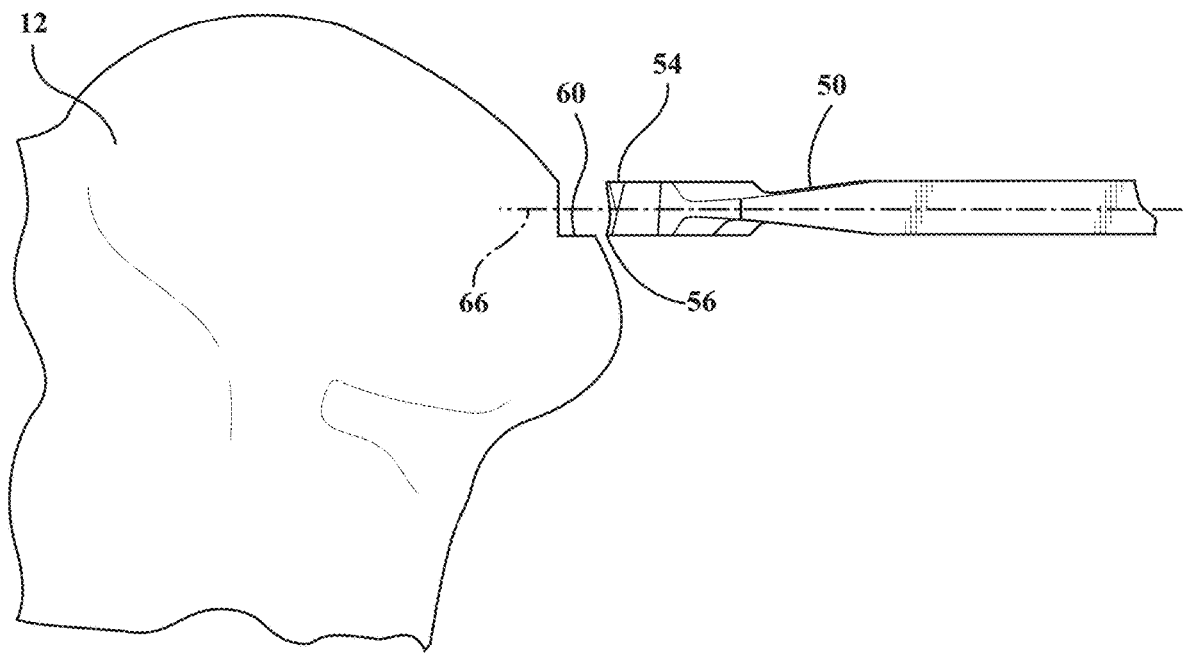
FIG. 5B is a side view of a blade of the robotic cutting system according to the embodiment illustrated in FIG. 5A.

In another exemplary embodiment, illustrated in FIGS. 5A and 5B, another cutting tool 30 may be used to form the initial notch 60 to limit skiving of the saw blade 50. In this case, the cutting tool 30 comprises a bur 62. The cutting tool 30 with the bur 62 may be initially connected to the robotic manipulator and configured to cut the hard tissue 12 until the cut reaches the desired depth to form the notch 60. The cut with the bur 62 can be carried out autonomously or manually in the manner previously described.

The bur 62 is used by the robotic cutting system 10 to create a desired profile in the hard tissue 12 to enable easier initial cutting of the saw blade 50 into the hard tissue 12 along the cutting plane 66. In the embodiment shown, the notch 60 is formed by the bur 62 to have a profile that both creates a face of hard tissue that's easier for the saw blade 50 to initially cut without skiving and creates a plateau to guide and support the saw blade 50 on the cutting plane 66 (see FIG. 5B). As illustrated in FIG. 5A, the bur 62 may be cylindrical such that the bur 62 forms the desired notch 60 in the hard tissue 12 when rotating about a rotational axis perpendicular to the cutting plane 66, e.g., an axis transverse to the cutting plane 66. Additionally, it is also contemplated, that the bur 62 may be spherical such that the bur 62 forms a rounded notch in the hard tissue 12 with the notch being concave in the outer surface to readily capture the saw blade 50 and prevent skiving by constraining the saw blade 50 from flexing. Various other bur configurations have been contemplated.

Once the notch 60 is formed, the robotic cutting system 10 will then finish the cut using the saw blade 50 in the same manner previously described. It is contemplated that the cutting tool 30 comprising the bur 62 may be uncoupled from the robotic manipulator once the notch 60 is formed so that the cutting tool 30 with the saw blade 50 can be fitted to the robotic manipulator. However, the cutting tool 30 with the bur 62 may remain coupled to the robotic manipulator in cases where two end effectors are capable of being attached to the robotic manipulator simultaneously. It is also contemplated that the cutting tool 30 is capable of receiving both the bur 62 and the saw blade 50 interchangeably so that only the bur 62 needs to be removed and the saw blade 50 attached. It is additionally contemplated that the initial cut done by the bur 62 may be performed with a manual cutting instrument without being connected to the robotic manipulator.

Figure 6A:
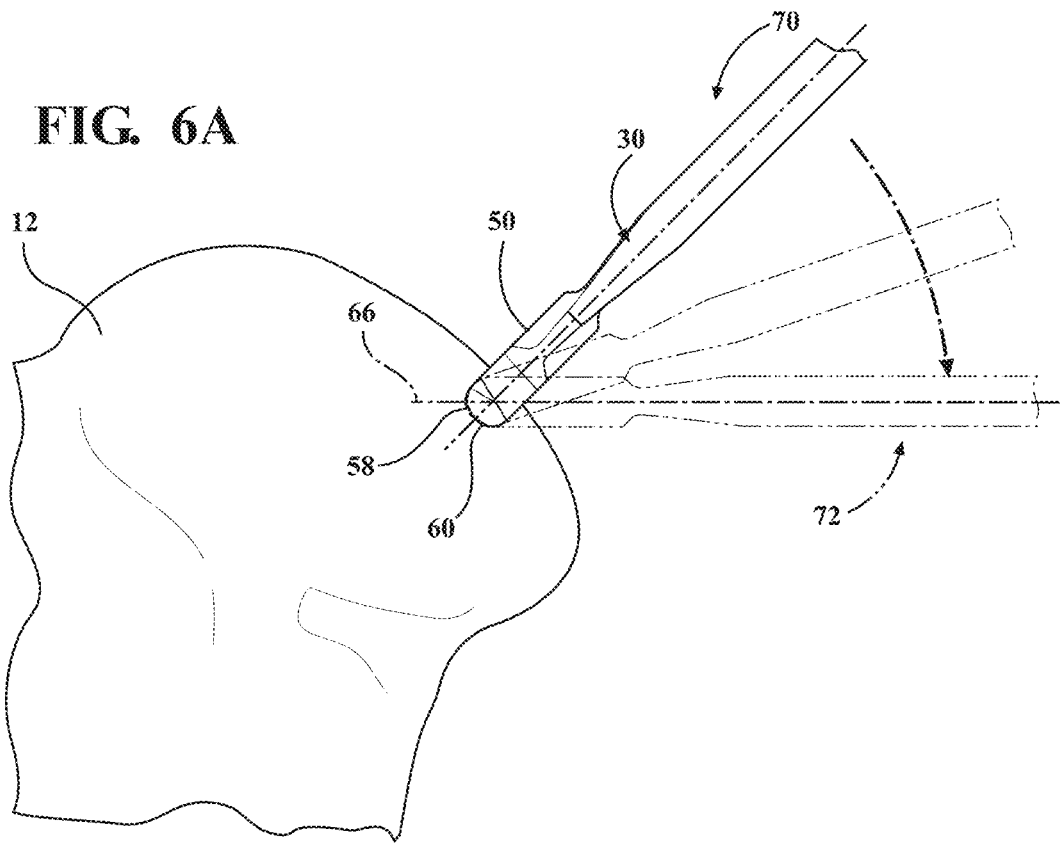
FIG. 6A is a side view of the cutting tool of the robotic cutting system according to yet another embodiment in the first orientation.
Figure 6B:
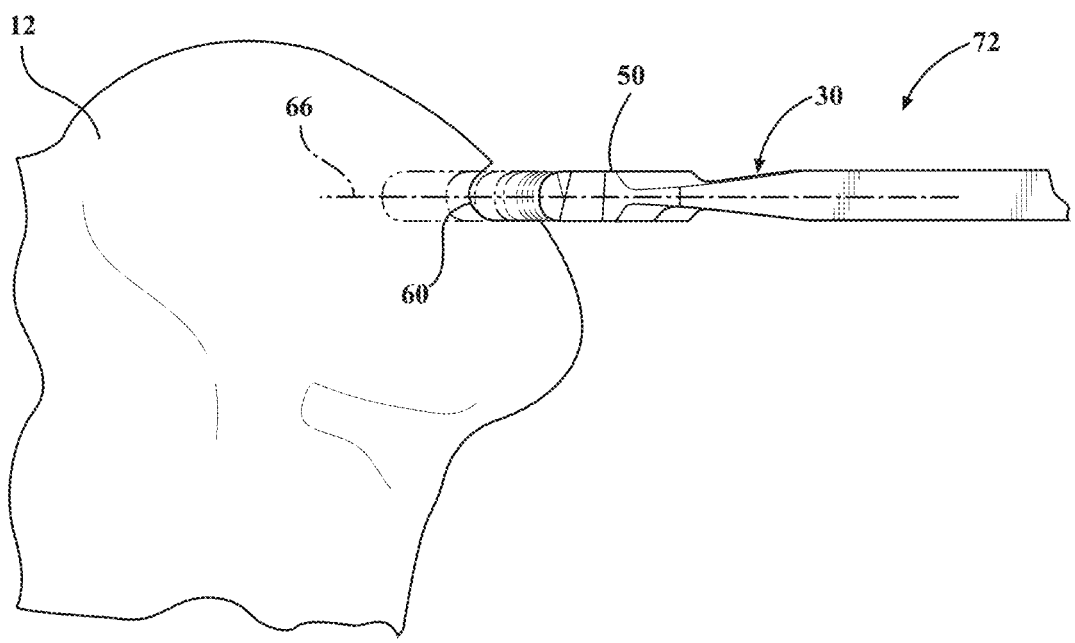
FIG. 6B is a side view of the cutting tool of the robotic cutting system according to the embodiment illustrated in FIG. 6A in the second orientation.

Referring to FIGS. 6A and 6B, the cutting portion 54 of the saw blade 50 may include a rounded tip 58 configured to engage the hard tissue 12. The rounded tip 58 is configured to create a rounded notch 60 in the hard tissue 12 during the cutting operation. The rounded notch 60 provides a starting point for the saw blade 50 to more easily complete the remainder of the cut along the cutting plane 66 by establishing a fulcrum about which the saw blade 50 can be reoriented to the cutting plane 66. Similar to the embodiment illustrated in FIGS. 3A and 3B, the cutting tool 30 begins the cut with the saw blade 50 in the first orientation 70 (FIG. 6A) which is normal to the outer surface of the hard tissue 12. The saw blade 50 remains in the first orientation 70 until the cut reaches a predetermined depth. Once the notch 60 is created, the saw blade 50 is rotated to the second orientation 72 (FIG. 6B), in line with the cutting plane 66, and the cut is finished. As shown in FIG. 6B, the saw blade 50 may be removed from the notch 60 before completing the final cut or the saw blade 50 may remain in the notch 60.

Figure 7A:
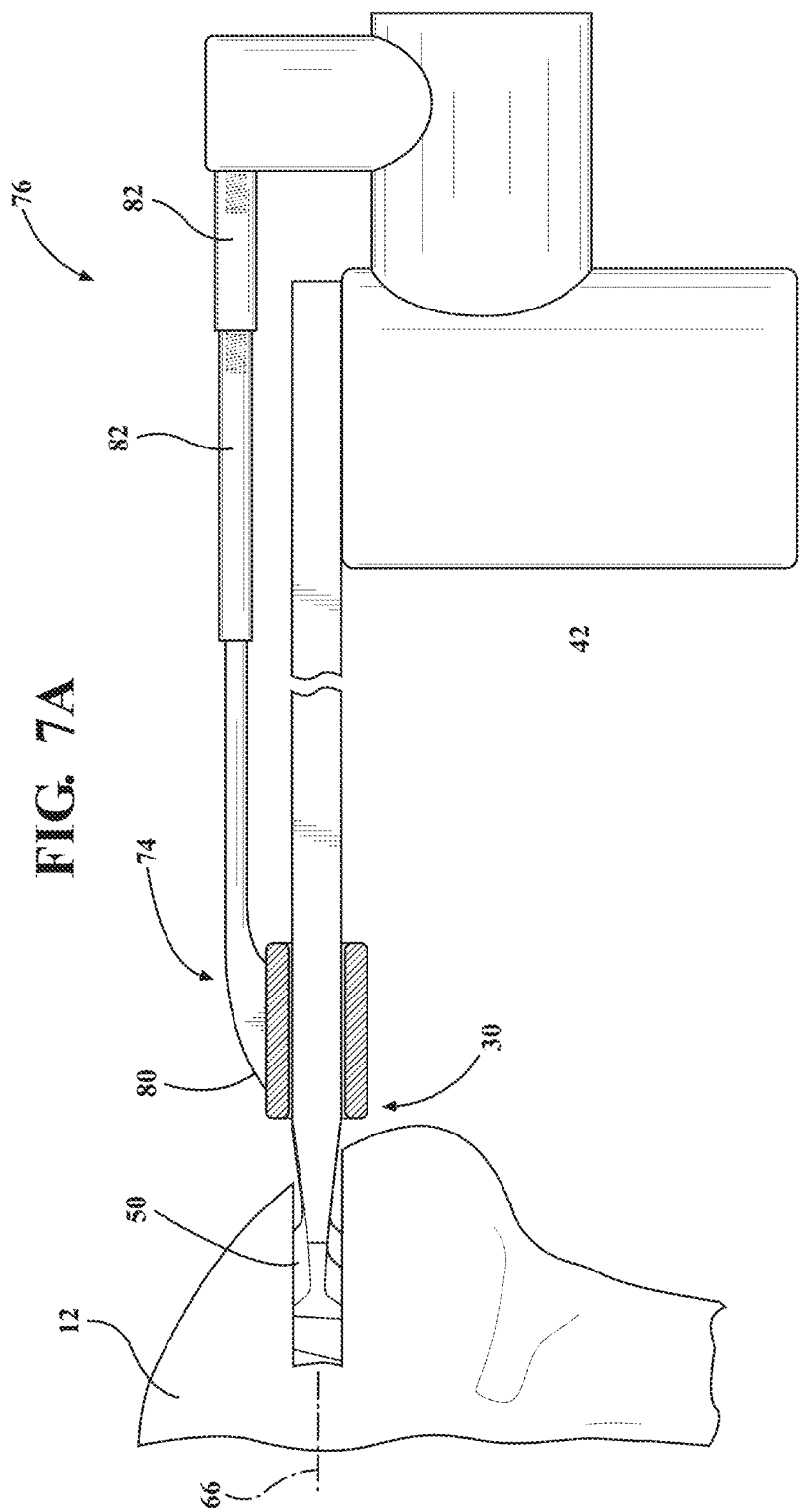
FIG. 7A is a side view of the cutting tool of the robotic cutting system having a blade guide in an extended position.
Figure 7C:
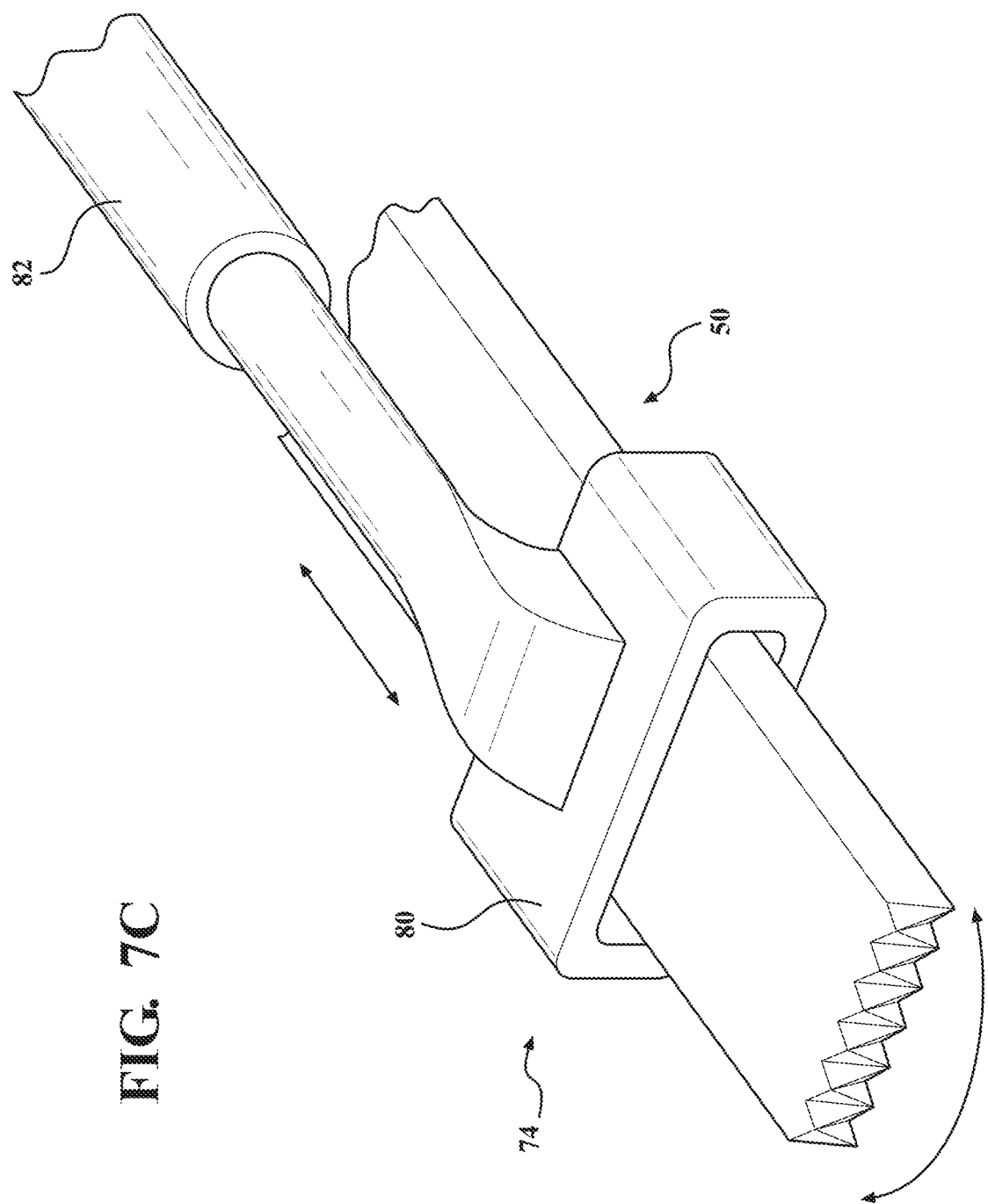
FIG. 7C is a perspective view of the blade guide illustrating the blade guide defining a passage being wider than a saw blade to allow oscillations of the saw blade in the passage.

In another exemplary embodiment, illustrated in FIGS. 7A and 7B, the robotic cutting system 10 further includes a rigid blade guide 74. The blade guide 74 is coupled to the housing 42 and is configured to provide support to the saw blade 50 during operation of the robotic cutting system 10. More specifically, the blade guide 74 has a rigidity which can provide stability to the saw blade 50 and withstand transverse forces from the hard tissue 12 acting on the saw blade 50 during operation that may otherwise cause skiving. Additionally, use of the blade guide 74 allows a thinner saw blade 50 to be used owing to the additional support being given to the saw blade 50 by the blade guide 74.

In the embodiment illustrated in FIGS. 7A and 7B, the blade guide 74 is a telescoping blade guide 74. More specifically, the blade guide 74 is configured to move between an extended position 76 (FIG. 7A) and a retracted position 78 (FIG. 7B). As illustrated in FIG. 7A, the blade guide 74 may include a first end 80 which is configured to receive the saw blade 50 of the cutting tool 30. It is contemplated that the first end 80 of the blade guide 74 may provide a passage sized to receive the saw blade 50 in a sliding manner such that the saw blade 50 is neatly disposed between and constrained from flexing by upper and lower walls of the blade guide 74, but is allowed to slide/oscillate within the blade guide 74 (see FIG. 7C). It is also contemplated that the blade guide 74 may engage the saw blade 50 in any manner configured to provide support and rigidity to the saw blade 50.

During operation, the blade guide 74 moves between the extended position 76 and the retracted position 78. In other words, at least a portion of the blade guide 74 may have telescoping members 82 configured to extend/retract the blade guide 74. Movement of the blade guide 74 may be controlled by the control system of the robotic cutting system 10. For example, an actuator A (e.g., electric motor) may be coupled to the telescoping members 82 or directly to the blade guide 74 to extend/retract the blade guide 74 (see FIG. 7B). For example, an electric linear actuator may be mounted to the housing 42 with an extendable rod connected to the blade guide 74 to extend/retract the blade guide 74. It is also contemplated that the blade guide 74 may be manually operated. In one embodiment (see FIG. 7A), the blade guide 74 includes a biasing device (e.g., springs S) which spring bias the blade guide 74 towards the extended position 76. The biasing device is arranged so that when the blade guide 74 engages the hard tissue 12 and the saw blade 50 is further driven into the hard tissue 12, the blade guide 74 retracts, albeit while continuously being biased toward the hard tissue 12 by the biasing device.

When cutting along the cutting plane 66 is desired, the cutting tool 30 is first aligned with the cutting plane 66 in the manner previously described with the blade guide supporting the saw blade 50 in the extended position 76. The saw blade 50 is then moved (either manually or autonomously as previously described) to engage the hard tissue 12 to begin the cut. During the cut, the blade guide 74 provides support to the saw blade 50. Moreover, as the saw blade 50 enters the hard tissue 12, the blade guide 74 telescopes from the extended position 76 (illustrated in FIG. 7A) to the retracted position 78 (illustrated in FIG. 7B) such that the blade guide 74 remains outside of the hard tissue 12 as the saw blade 50 enters deeper into the hard tissue 12. In the case of using an actuator to move the blade guide 74, the navigation system 13 monitors movement of the saw blade 50 relative to the hard tissue 12 and the control system operates the actuator A as desired to move the blade guide 74 in a coordinated manner so that the saw blade 50 is continuously supported during at least the initial cut into the hard tissue 12 adjacent to the outer surface. The saw blade 50 finally finishes the cut along the cutting plane 66.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A robotic cutting system comprising:
   a robotic manipulator;
   a cutting tool to be coupled to the robotic manipulator, the cutting tool having a saw blade configured to cut a bone along a cutting plane; and
   a controller coupled to the robotic manipulator to control the robotic manipulator and the cutting tool to:
   perform an initial stage of cutting along an initial plane prior to performing a final stage of cutting along the cutting plane, the initial plane being at a different orientation than the cutting plane, wherein the controller is configured to control the robotic manipulator and the cutting tool to facilitate cutting along the initial plane with the saw blade to create a notch for the saw blade;
   facilitate reorientation of the saw blade from the initial plane to the cutting plane; and
   perform the final stage of cutting along the cutting plane whereby the notch created along the initial plane is configured to capture the saw blade to limit skiving of the saw blade during the final stage of cutting.

2. The robotic cutting system of claim 1, wherein the controller is configured to control the robotic manipulator and the cutting tool to facilitate reorienting the saw blade while the saw blade is located in the notch.

3. The robotic cutting system of claim 2, wherein the controller is configured to control the robotic manipulator and the cutting tool to facilitate reorienting the saw blade while the saw blade is oscillating.

4. The robotic cutting system of claim 1, wherein the initial plane is defined by a first virtual boundary and the controller is configured to control the robotic manipulator to perform the initial stage of cutting along the initial plane by constraining movement of the saw blade using the first virtual boundary.

5. The robotic cutting system of claim 4, wherein the cutting plane is defined by a second virtual boundary, different than the first virtual boundary, and the controller is configured to deactivate the first virtual boundary after forming the notch.

6. The robotic cutting system of claim 1, wherein the controller is configured to control the robotic manipulator and the cutting tool to facilitate cutting along the initial plane by at least one of: autonomously moving the cutting tool; and constraining movement of the cutting tool.

7. The robotic cutting system of claim 1, wherein the controller is configured to control the robotic manipulator and the cutting tool to reorient the saw blade from the initial plane to the cutting plane by at least one of: autonomously moving the cutting tool; and constraining movement of the cutting tool.

8. The robotic cutting system of claim 1, wherein the controller is configured to autonomously align the saw blade with the initial plane.

9. The robotic cutting system of claim 1, wherein the initial plane is defined as being normal to an outer surface of the bone.

10. The robotic cutting system of claim 1, wherein the cutting tool comprises an oscillating saw.

11. The robotic cutting system of claim 1, wherein the saw blade has a rounded cutting end.

12. A robotic cutting system comprising:
    a robotic manipulator;
    a cutting tool to be coupled to the robotic manipulator, the cutting tool having a saw blade configured to cut a bone along a cutting plane;
    a bur to be coupled to the robotic manipulator; and
    a controller coupled to the robotic manipulator to control the robotic manipulator to:
    perform, with the bur, an initial stage of burring a notch into the bone; and
    perform, with the saw blade, a final stage of cutting along the cutting plane whereby the notch created during the initial stage of burring is configured to capture the saw blade to limit skiving of the saw blade during the final stage of cutting.

13. The robotic cutting system of claim 12, wherein the initial stage is defined by a first virtual boundary and the controller is configured to control the robotic manipulator to perform the initial stage of burring a notch into the bone by constraining movement of the bur using the first virtual boundary.

14. The robotic cutting system of claim 13, wherein the final stage of cutting is defined by a second virtual boundary, different than the first virtual boundary, and the controller is configured to deactivate the first virtual boundary after burring the notch.

15. The robotic cutting system of claim 12, wherein the controller is configured to control the robotic manipulator and the bur to perform the initial stage of burring by at least one of: autonomously moving the bur; and constraining movement of the bur.

16. The robotic cutting system of claim 12, wherein the controller is configured to control the robotic manipulator and the cutting tool to perform the final stage of cutting by at least one of: autonomously moving the cutting tool; and constraining movement of the cutting tool.

17. The robotic cutting system of claim 12, wherein the controller is configured to control the robotic manipulator to perform the initial stage of burring about an axis perpendicular to cutting plane.

18. The robotic cutting system of claim 12, wherein the cutting tool and the bur are concurrently coupled to the robotic manipulator such that the cutting tool is coupled to the robotic manipulator while the controller controls the robotic manipulator to perform the initial stage of burring a notch into the bone, and the bur is coupled to the robotic manipulator while the controller controls the robotic manipulator to perform the final stage of cutting along the cutting plane.

19. The robotic cutting system of claim 12, wherein:
the bur is coupled to the robotic manipulator exclusive of the cutting tool such that the cutting tool is uncoupled from the robotic manipulator while the controller controls the robotic manipulator to perform the initial stage of burring a notch into the bone; and
the cutting tool is coupled to the robotic manipulator exclusive of the bur such that the bur is uncoupled from the robotic manipulator while the controller controls the robotic manipulator to perform the final stage of cutting along the cutting plane.

20. The robotic cutting system of claim 12, wherein the cutting tool is configured to receive the saw blade.

21. The robotic cutting system of claim 12, wherein the cutting tool is configured to receive the bur.

* * * * *